United States Patent [19]

Hall

[11] 4,151,615

[45] May 1, 1979

[54] PROSTHETIC PATELLO-FEMORAL JOINT

[76] Inventor: Thomas D. Hall, 821 Hudson Rd., Glenview, Ill. 60025

[21] Appl. No.: 811,431

[22] Filed: Jun. 29, 1977

[51] Int. Cl.² .............................................. A61F 1/24
[52] U.S. Cl. ...................................... 3/1.91; 128/92 C
[58] Field of Search ..................... 3/1.91, 1.913, 1.911; 128/92 C

[56] References Cited

U.S. PATENT DOCUMENTS

| | | | |
|---|---|---|---|
| 3,806,961 | 4/1974 | Muller | 3/1.913 |
| 3,878,566 | 4/1975 | Bechtol | 3/1.91 |
| 4,007,495 | 2/1977 | Frazier | 3/1.91 |
| 4,052,753 | 10/1977 | Dedo | 3/1.91 X |

*Primary Examiner*—E. H. Eickholt

[57] ABSTRACT

A prosthetic patello femoral joint includes a patellar and a femoral component designed to replace the articular surfaces of this joint in normal relationship with each other and with the patella and femur thus preserving the normal bio-mechanics of the joint. The patellar component is adapted to be secured to the remaining portion of the patella after resection of sufficient patella to permit the prosthetic surface for articulation to assume a relatively normal position in relationship to the remaining patella. The femoral component is adapted to be secured within a resection of the femur of sufficient width and depth to permit its insertion with its articulating surface as a replacement for the diseased surface in normal relationship with the remainder of the femur. The patellar component includes a slightly convex surface much smaller than but conforming to the concavity of the femoral conponent for the purpose of distributing the compressive forces evenly. The femoral component surface conforms to the slightly concave surface of the normal femur and is much wider than the patellar component, permitting the patella to move from side to side at will in it longitudinal progression.

5 Claims, 10 Drawing Figures

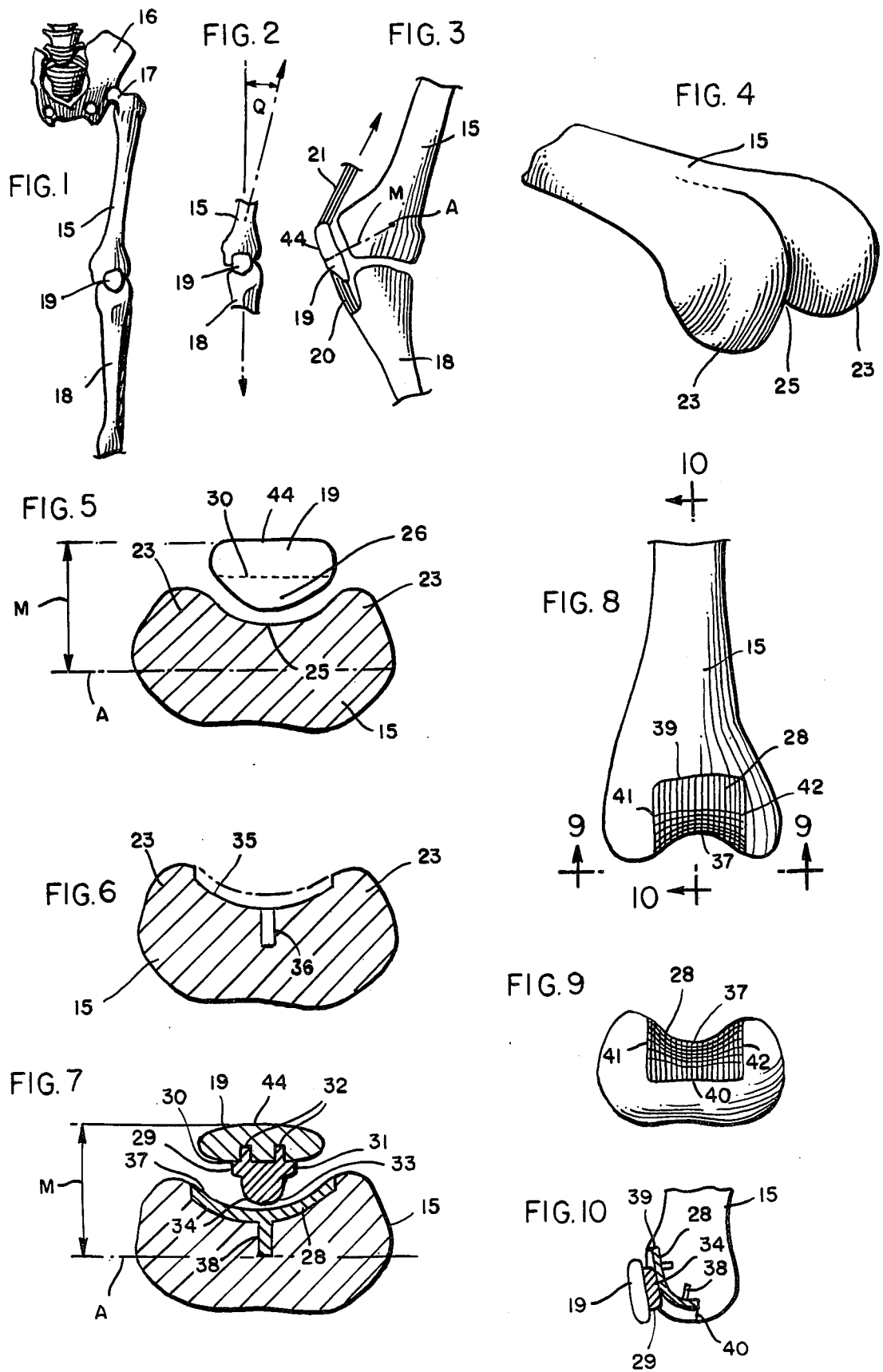

PROSTHETIC PATELLO-FEMORAL JOINT

BACKGROUND AND SUMMARY

This invention relates to a knee joint, and, more particularly, to a patellar-femoral joint.

There are two joints in the knee which permit movement between the femur and the tibia. A weight-bearing joint occurs between the condyles of the femur and the superior end of the tibia, and a joint occurs between the patella or knee cap and the femur. The patellar ligament extends between the patella and the tibia and fixes the distance between the patella and the tibia. Accordingly, as the leg is flexed and extended, the patella slides up and down in the intercondylar groove of the femur. This is a so called gliding joint, and although not a true weight bearing joint is also subject to various forms of arthritis. As the articular surface of the patella thins and roughens either as a result of wear and tear or due to injury, friction increases, function decreases and pain occurs.

Not too many years ago the function of the patella was poorly understood and many believed that it was a vestige from some predecessor in the evolutionary tree and really had no function in man. This philosophy popularized the treatment of patellar-femoral arthritis by the removal of the patella. This is still the most commonly used treatment because there has been nothing else that provides better results.

An analysis of those knees that had been subjected to the removal of the patella revealed the major disability was a weakness in the last few degrees of extension. It is now appreciated that the patella functions both as a pulley to change the force vectors of the pull of the anterior thigh muscles on the knee and as a fulcrum for the lever action required. An additional consideration was that after the removal of the patella, the remaining tendon continued to move through the intercondylar notch and continued to worsen the arthritis on that surface.

In the normal function of the knee the patella rests in a concave groove between the condyles of the femur which is called the patellar bed of the distal femur. This bed and the opposing under surface of the patella are covered with articular cartilage and subject to arthritis. The opposing surfaces of this joint are not in contact with the weight bearing portion of the knee joint.

The intercondylar groove aids in stabilizing the patella and prevents medial and more significant lateral displacement of the patella. The tendency to laterally displace is inherent to the normal anatomy of the patellar ligament attachment and the formation of an angle between the quadriceps muscle pull and the site of the attachment, called the Q Angle.

With motion of the knee the patella moves through the intercondylar groove in articulation with the femoral bed and in so doing a different portion of the patella is in contact with a different portion of the bed during various positions. In the extended position the inferior portion of the patella is in contact with the superior part of the bed. In flexion the superior part of the patella is in contact with the inferior part of the patellar bed.

I have devised the construction of two components to be utilized for the total replacement of the patellar-femoral joint. This joint although not a weight bearing joint is subject to considerable compression forces between component bones. This force is exerted because of the pulley like function of the patella in changing the force vector of the muscle pull of the thigh muscles. Because of the angular relationship between the direction of the pull of the quadriceps muscle on the patella and that of the patella ligament (the Q Angle) and the fact that knee joint flexion and extension is not a pure hinge movement but has associated rotation means that a simple groove could not retain the patellar component without considerable restrictive force with adds friction and wear. Because the shortest distance between two points is a straight line, as pull is applied on the patella during extension, there would be a lateral shift of the patellar which would tend to displace it from the groove.

Rather than a groove, I propose a femoral component which would replace that portion of the surface of the femur which comes into contact with the patellar component. The femoral component has a concave surface which engages the patellar component and which is substantially wider than the patellar component so that the patellar component can move laterally and medially over the concave surface.

DESCRIPTION OF THE DRAWING

The invention will be explained in conjunction with an illustrative embodiment shown in the accompanying drawing, in which FIG. 1 is a front elevational view of a human femur, patella, and tibia;

FIG. 2 is a fragmentary view of a portion of FIG. 1 illustrating the Q angle;

FIG. 3 is a schematic side view of the femur, patella, and tibia showing the direction of pull on the patella during extension of the tibia;

FIG. 4 is a fragmentary perspective view of the inferior end of the femur;

FIG. 5 is a transverse sectional view through the femur showing the relationship between the patella and the femur;

FIG. 6 is a sectional view through the femur showing the femur resected in preparation for securing the femoral component;

FIG. 7 is a view similar to FIG. 5 showing the patellar and femoral components secured to the resected patella and femur;

FIG. 8 is a front elevational view of the femur and femoral components;

FIG. 9 is a bottom plan view of the femur and femoral component taken along the line 9—9 of FIG. 8; and FIG. 10 is a vertical sectional view through the femur and the patella as would be seen along the line 10—10 of FIG. 8.

DESCRIPTION OF SPECIFIC EMBODIMENT

FIGS. 1-3 illustrate the relationship between the femur, tibia, and patella of a human. The femur 15 attaches laterally on the pelvis 16 through a ball and socket joint 17, and the femur extends downwardly and medially (i.e., toward the midline of the body) from the pelvis. The tibia 18 supports the inferior end of the femur and extends vertically downwardly therefrom. The patella 19 is connected to the tibia by the patella ligament 20, and the tibia is extended from a flexed position (FIG. 3) by a pulling force exerted by the quadriceps muscle 21.

Referring to FIG. 4, the inferior end of the femur includes two somewhat ball-shaped condyles 23 and 24, and an intercondylar groove 25 extends between the condyles at both the anterior and inferior aspects. The intercondylar groove provides a generally concave surface which receives a generally convex projection 26 on the patella (FIG. 5). The intercondylar groove stabilizes the patella and prevents medial and lateral displacement as the patella moves up and down relative to the condyles when the tibia is extended and flexed. Because of the angle between the femur and the tibia, there is an angle between the direction of the pull on the patella by the quadriceps muscle and the direction of the pull on the patella by the patellar ligament. This angle is known as the Q angle (indicated in FIG. 2) and is about 10° to about 15°. As the patella is pulled upwardly within the intercondylar groove by the quadriceps muscle during extension, the quadriceps muscle exerts a force on the patella which tends to move the patella laterally, i.e., to the right as viewed in FIG. 2.

When the joint between the patella and the femur becomes worn or damaged, this joint can be replaced with a prosthetic joint comprising a femoral component 28 (FIGS. 7-10) and a patellar component 29 (FIGS. 7 and 10). The patella and the femur are first resected to remove a sufficient amount of the patella and femur so that the prosthetic parts can be secured without causing significant change in the patellar-femoral relationship and the relationship between the quadriceps muscle and patellar ligament with respect to the patella which would affect the bio-mechanics of patello-femoral function.

In FIG. 5 the portion of the patella which is resected is indicated by the dashed line 30. The patellar component 29 includes a relatively flat base 31 (FIG. 6) which includes a plurality of anchoring projections or pins 32 which are inserted into suitable holes formed in the remaining portion of the patella. The patellar component can be fixed to the patella with a bio-compatible cement such as methyl merthacolate, and the pins 32 strengthen the securement of the patellar component to the patella. The posterior surface 33 of the patellar component, i.e., the surface which faces the femur, has a projection 34 having a convex transverse cross section (FIG. 7). The longitudinal cross section of the patellar component is shown in FIG. 10, and the convex surface extends longitudinally for a substantial portion of the length of the patella.

The resected femur is illustrated in FIG. 6. The resected area 35 extends laterally and medially away from the center of the intercondylar groove into the condyles 23, and one or more holes 36 extend posteriorly into the femur. The femoral component 28 has a concave anterior surface 37 which has a contour substantially the same as the contour of the anterior surface of the undamaged femur, and one or more anchoring pins 38. The femoral component is shown cemented in place in FIGS. 7-10.

The femoral component has a superior end 39, an inferior end 40, and a pair of side edges 41 and 42. The femoral component has a somewhat J-shaped longitudinal cross section (FIG. 10) which is provided by a relatively straight superior end portion and an arcuate inferior portion.

The material of the patellar component and the femoral component must be able to withstand the compression forces exerted between the patella and the femur and have relatively low friction. I prefer to use one of the available biologically inert stainless steel alloys for one of the components and polyethylene for the other component.

The lateral dimension of the convex projection 34 of the patellar component is substantially less than the lateral dimension of the concave surface 37 of the femoral component, and the radius of curvature of the convex surface is substantially less than the radius of curvature of the concave surface. Accordingly, the patellar component has a smaller surface area which comes into contact with the femoral component than vice versa. As the convex surface of the patellar component moves up and down over the concave surface of the femoral component during extension and flexion of the tibia, the patella is not confined within a narrow groove in the femoral component but is instead permitted to wander toward either side of the femoral component by virtue of the smoothly curved concave surface. The patellar component remains in contact with the femoral component throughout its movement, and the patellar component can therefore always push against the femoral component to bring the tibia to full extension. Because of the substantial dimension of the femoral component between the superior edge 39 and the inferior edge 40, the patellar component will remain in contact with the femoral component throughout flexion and extension.

The amounts of patella and femur which are resected are sufficient in relationship to the prosthetic patellar and femoral components to preserve the normal moment arm between the patella and axis of rotation of the tibia. In FIGS. 3 and 5 A represents the axis about which the tibia rotates. The perpendicular distance between this axis and the anterior surface 44 of the patella to which the quadriceps muscle 21 and ligament 20 are attached is the moment arm M. If the patella is moved away from the axis by inserting a prosthesis between the patella and the femur, the moment arm and therefore the biomechanics of the knee will change.

The amount of patella which is removed by resection is that which is sufficient to permit the articulating surface of the patellor prosthesis to be in normal relationship with the remainder of the patella and thus maintain the same moment arm. Similarly, the amount of femur which is resected in relation to the femoral prosthesis preserves the normal moment arm. This is illustrated in FIG. 7 in which the moment arm M is the same as the moment arm M in FIG. 5.

While in the foregoing specification a detailed description of a specific embodiment of the invention was set forth for the purpose of illustration, it will be understood that many of the details hereingiven may be varied considerably by those skilled in the art without departing from the spirit and scope of the invention.

I claim:

1. A knee joint comprising a patellar component and a femoral component, the patellar component having an anterior surface adapted to be secured within a resection in the patella of a patient, and a posterior surface having a convex portion sized to fit into the intercondylar groove of the femur of the patient; the femoral component having a posterior surface adapted to be secured within a resection in the femur of the patient, and an anterior surface having a concave portion extending across the intercondylar groove, and a pair of generally parallel side edges; the convex portion of the patellar component being engageable with the concave portion of the femoral component, the width of the concave portion of the femoral component between the side edges thereof being substantially greater than the width of the convex portion of the patellar component whereby the patellar component can move from one side of the femoral component to the other.

2. The structure of claim 1 in which the femoral component has a generally J-shaped cross section in a plane which extends through the femoral component parallel to the side edges.

3. The structure of claim 2 in which the superior portion of the concave portion of the femoral component is relatively straight, and the inferior portion of the concave portion of the femoral component is arcuate.

4. The structure of claim 1 in which the side edges of the femoral component extend laterally and medially into the condyles of the femur.

5. A method of replacing a patellar-femoral joint with a prosthetic patellar-femoral joint comprising the steps of:

resecting the posterior surface of the patella, fitting a patellar prosthetic component to the resected portion of the patella and securing the patellar prosthetic component to the patella, the dimensions of the patellar prosthetic component corresponding generally to the dimensions of the resected portion of the patella and the patellar component having a posterior surface having a convex portion sized to fit into the intercondylar groove of the femur, resecting the anterior surface of the femur from one condyle of the femur to the other condyle, fitting a femoral prosthetic component to the resected portion of the femur and securing the femoral prosthetic component to the femur, the dimensions of the femoral prosthetic component corresponding generally to the dimensions of the resected portion of the femur and the femoral component having an anterior surface having a concave portion extending across the intercondylar groove, and a pair of generally parallel side edges, the posterior surface of the patella and the anterior surface of the femur being resected sufficiently to maintain the moment arm of the tibia substantially constant before and after the patellar and femoral prosthetic components are secured, the convex portion of the patellar component being engageable with the concave portion of the femoral component, the width of the concave portion of the femoral component between the side edges thereof being substantially greater than the width of the convex portion of the patellar component whereby the patellar component can move from one side of the femoral component to the other.

* * * * *